(12) United States Patent
Mirochnik et al.

(10) Patent No.: US 8,167,989 B2
(45) Date of Patent: May 1, 2012

(54) COMPOUND OF DI (NITRATE) ACETYLACETONATOBIS (1,10-PHENANTHROLINE) LANTANOID (III), APPLICABLE FOR LUMINESCENT ADDITIVE TO INK, AND INK FOR HIDDEN MARKING OF VALUABLES DESCRIPTION

(75) Inventors: Anatoliy Grigor'evich Mirochnik, Vladivostok (RU); Vladimir Egorovich Karacev, Vladivostok (RU)

(73) Assignee: Samsung Electronics Co., Ltd., Suwon-Si (KR)

( * ) Notice: Subject to any disclaimer, the term of this patent is extended or adjusted under 35 U.S.C. 154(b) by 685 days.

(21) Appl. No.: 12/271,145

(22) Filed: Nov. 14, 2008

(65) Prior Publication Data
US 2009/0145328 A1 Jun. 11, 2009

(51) Int. Cl.
*C09D 11/00* (2006.01)
*C09K 11/06* (2006.01)
*C07F 5/00* (2006.01)

(52) U.S. Cl. .......... 106/31.14; 252/301.16; 252/301.35; 534/15; 534/16

(58) Field of Classification Search ............... 106/31.14, 106/31.32, 31.64; 252/301.16, 310.35; 534/15, 534/16
See application file for complete search history.

(56) References Cited

U.S. PATENT DOCUMENTS

| 4,443,380 A * | 4/1984 | Yamazoe et al. ................. 534/16 |
| 4,572,803 A * | 2/1986 | Yamazoe et al. ................. 534/16 |
| 5,095,099 A * | 3/1992 | Parkinson et al. ............... 534/15 |
| 7,811,676 B2 * | 10/2010 | Kathirgamanathan et al. ............................. 428/690 |
| 2002/0015965 A1 * | 2/2002 | Sweeting ......................... 534/15 |

OTHER PUBLICATIONS

"Influence of the Nature of Complexing Ion on the Thermoluminescent Properties of the RE Coordination Compounds"; Karasev et al.; Jan. 1999; Abstract only.*

* cited by examiner

*Primary Examiner* — Helene Klemanski
(74) *Attorney, Agent, or Firm* — Stanzione & Kim, LLP

(57) ABSTRACT

The invention refers to new chemical compounds belonging to the known class of REE mixed ligand complexes, namely, to the compound of di-(nitrate)acetylacetonatobis (1,10-fenantrolin)lanthanide (III) of the general formula [Ln(NO$_3$)2Acac(Phen)2]*H20, where Ln is TbxEr1-x, Acac is acetylacetonate-ion, Phen is 1,10-fenantrolin in the form suitable for application as a luminescent additive to ink for the hidden marking the valuables to provide protection against forgery. Such additive has three protective features suitable for automatic control independently of each other. The first protective feature is the ability to luminescence in green light under the impact of UV-radiation. The second protective feature is the ability to luminescence in green light under the impact of X-rays. The third protective feature is the Thermo-luminescence, which means the ability to accumulate for indefinite time span the energy of UV- and X-rays with subsequent green light emission at heating. It allows univocal identification of valuables and improves the protection efficiency.

3 Claims, No Drawings

COMPOUND OF DI (NITRATE) ACETYLACETONATOBIS (1,10-PHENANTHROLINE) LANTANOID (III), APPLICABLE FOR LUMINESCENT ADDITIVE TO INK, AND INK FOR HIDDEN MARKING OF VALUABLES DESCRIPTION

CROSS-REFERENCE TO RELATED APPLICATIONS

This application claims priority of Russian Patent Application No. 2007-136983, filed on Dec. 5, 2007, in the Russian Patent Office, the disclosure of which is incorporated herein in its entirety by reference.

BACKGROUND OF THE INVENTION

1. Field of the Invention

The invention falls into chemistry elemental organic compounds, more particularly, to new chemical compounds of the known class—mixed ligand complexes of rare earth elements (REE), namely, to compounds di-(nitrate)acetylacetonatobis (1,10-phenanthroline) lanthanide (III) where lanthanide represents $Tb_xEr_{1-x}$, applicable for use as a luminescent additive in ink for hidden marking the valuables, which ink can be applied in verification of authenticity of documents, excise tags, banknotes and other securities and products.

2. Description of the Related Art

Among the known REE complexes one can find a heat sensitive luminophor energized by UV-radiation at $\lambda_{energ}$ equal to 335 nanometers, which luminophor is an element consisting of the europium salts and the cinnamic acid (JP patent application No 57-83580, published 25 May 1982).

Also known is a luminescent composition comprising a REE crystal salt and the organic carboxylic acid, featuring bright luminescence at excitation by an electron beam, X rays or UV-radiation. The REE is, commonly, represented by Ce, Pr, Nd, Sm, Eu, Tb, Dy, Ho, Tm or Yb, wherein an organic carboxylic acid is represented by the benzoic, o-toluil or n-phthalic acid (JP patent application No 57-18779, published 30 Jan. 1982).

However the said compounds are not capable of accumulating the energy of an ionizing radiation and therefore cannot be used as the thermo-luminophors registering radiation previous impact.

Class of mixed ligand complexes of rare earths elements comprises pentanitrate REE 1,10-phenantrolone, where REE-Tb or Dy, or Ho (Shchelokov P. H., Bolotova G. T, Perov V. I, Evstafieva O. N, Nitrate complexes of rare earths with 1,10-phenantrolone in outer sphere, G. inorganic chemistry, 1988, v. 33, No 4, p. 867).

The said complexes of REE are structural analogues of the claimed compounds, however they have very weak luminescence, cannot either accumulate energy or be used as a thermo-luminophor for registration of UV-radiation and X-rays.

The state-of-the-art, by application mode, includes the technical solutions presented in the following sources. Composition for the hidden data recording, comprising solution A containing a luminophor, a binding substance and an organic solvent, and, in addition, solution B, also the containing a different luminophor, a binding substance and an organic solvent, is known, wherein the A/B ratio is within the range of 1:10 to 10:1. For producing a hidden data recording the solution A is placed on a substrate, kept on till evaporation of the solvent followed by generation of a film, then the substrate is processed by the solution B, dried and illuminated by UV-light (see RU No 2057782, published 10 Apr. 1996). The luminophors in this case are represented by the organic compounds creating molecular solutions in organic solvents. The identification data embedded on the substrate in such a manner are visualized at illumination of the surface by UV-radiation, for example, by a mercury lamp.

Also known is the use of colorless ink composed of a solution of an organic luminophor for marking a document with machine-readable tags indiscernible in the visible light. The colorless inks are capable of being visualized on a paper at its illumination by an ultraviolet light (patent application RU No 98101973, published 10 Jan. 2000).

Use of organic luminophors as ink for marking enables producing a bright and high-contrast image at visualization of the recorded identification data, however, the common drawback of such technical solutions consists in the presence of a wide spectrum of fluorescence, intrinsic to all organic luminophors, which feature complicates verification of documents. Besides, the organic compounds do not luminance under X-rays (there is no bright emission), which feature limits the protection degree in case of use of organic luminophors for marking.

This is why the most commonly used luminophors are those which are capable of emitting radiation only in a very narrow range of the wave-length, for example, the compounds of rare earths. The advantage of such luminophors, by comparison with the luminophor emitting the radiation in a wide range of wave-length, consists in that their radiation has more particular spectrum in comparison with the spectrums of radiation of other substances, therefore such luminophors should be recognized as more reliable at automatic control of authenticity of documents (WO 00/39397, published 6 Jul. 2000; patent RU No 2249504, published 10 Apr. 2005).

In the RU patent No 224 9504 the combination of substances with two automatically controllable features for protection of important documents against forgery is proposed. An important document is characterized by the presence of, at least, two luminophors which luminescent features can be automatically controlled independently of each other. The first luminophor irreversibly loses its luminescent capability at the first temperature. The second luminophor irreversibly loses the luminescent capability at the second temperature. The first and/or the second temperature exceed the temperature of inflammation of the important document. It allows univocal identifying the important document both by its appearance and by its ashes and excludes the possibility of illegal regeneration of the materials used for protection against forgery for the producing duplicates of the securities.

In particular cases of embodiment of the invention under the RU patent No 2249504, the first luminophor is, preferably, represented by an inorganic luminophor, the second luminophor is an organic luminophor, and, in a preferable embodiment, such luminophor is represented by the dark blue methylene.

In another alternative the first and second luminophors are the inorganic luminophors containing crystal substances, of which the lattice of the matrix comprises alloying admixtures REE. Preferably, a rare-earth element is chosen from the group comprising neodymium, ytterbium, praseodymium, erbium and holmium. In the preferable embodiment the second luminophor is $ZnS:CuCl$, and the first luminophor is $Y_3Al_5O_{12}:Tb$.

The drawback of the said combination of substances consists in low intensity of the luminescence and presence only two levels of protection.

Also known is a fluorescent aqueous stamp mastic containing a water-soluble fluorescent coloring agent emitting light at the wave lengths within the range of 200 to 700 nanometers due to action of radiation with the wave lengths within the range of 200 to 700 nanometers, a water-soluble not fluorescent coloring agent, a binding agent represented by polyethylene glycol with molecular weight of 200 to 60000, the low molecular alcohols and water and, in addition, a water-soluble organic luminophor with the radiation range of 450 to 500 nanometers and with a wide range of excitation of some 200 to 400 nanometers, and also in the capacity of europium β-diketonat-europium tris-tenoiltriftoratsetononat (RU patent No 2220997, published 10 Jan. 2004).

The main drawbacks of the stamp mastic for hidden data recording consist in that they multi-component and provide for one protection level only, which makes this mastic inapplicable for reliable protection of products against forgery. Photo stability of europium used in the mastic is moderate, its spectrum is generally known for a long time.

The luminescent composition for marking securities, based on fine-crystalline fluorides of rare earths and oxy-halogenids of rare earth elements (FR patent No 2554122, published 3 May 1985), the size of the crystalline particles reaches some 5 to10 microns, that is, basically, not applicable in most printing techniques. Besides, luminophor based on oxy-halogenids of rare earths, change their characteristics with time passing. At that, the marking executed by such composition, is easily visualized by means of generally known methods, which feature reduces efficiency of the passive protection of the documents against forgery.

Also known is the luminescent composition for marking securities, containing fine-crystalline gadolinium oxifuldid activated by terbium, and yttrium oxifuldid activated by ytterbium and erbium, taken in the ratio of some 2:1 to 1:2 (RU patent No) 2253665, published 0.06.2005). The size of crystalline particles of the said luminophors does not exceed 1.5 microns. The prepared composition is added to a printing ink and is used for covering a surface to be marked, by usual printing technique, in the form of a label invisible at usual illumination. The label is visualized when illuminated by a light source emitting infra-red and/or ultraviolet radiation which provokes its light emission in green color. Then, the identification of the document takes place and the conclusion about its authenticity or falsification is made.

It should be noted, that all above compositions for marking securities and important documents include, at least, two components are provide for one or two levels of protection.

At that, the most essential drawback of the luminophors based on inorganic REE compounds consists in their low, in comparison with organic REE complexes, intensity of light emission.

The most similar solution-analogue to the claimed compound, by chemical composition and structure, and also by application, is the compound belonging to the class of REE mixed ligand complexes di-(nitrat-acetyl-acetonate)-1,10-phenanthroline lanthanide (III) 1,10-phenanthroline, where lanthanide—Tb or Dy.

The said compounds can be used as thermo-luminophors for detectors and ionizing radiation dosimeters (the USSR inventor's certificate No 1679769, published 27 Mar. 1996).

At the same time, in case of their use for marking valuables, these known compounds can offer only two levels of protection, at that, they have inadequate intensity of thermo-luminescence.

SUMMARY OF THE INVENTION

The problem to be solved by the claimed invention consists in generation of di-(nitrat)acetylacetonatobis (1,10-phenan-throline) lanthanide (III) compounds with common formula $[Ln(NO_3)_2Acac(Phen)_2]*H_2O$, where Ln is $Tb_xEr_{1-x}$, Acac is acetylacetonate-ion, Phen is 1,10-phenanthroline, possessing an effective luminescence and X-ray-luminescence, and also having better capability of accumulating light-sum under the impact of UV- and X-rays and displaying it at heating (thermo-luminescence).

The said problem is solved by creating compounds containing di-(nitrate)acetylacetonatobis (1,10-phenanthroline) lanthanide (III) of the general formula $[Ln(NO_3)_2Acac(Phen)_2]*H_2O$, where Ln is $Tb_xEr_{1-x}$, Acac is acetylacetonate-ion, Phen is 1,10-phenanthroline, possessing properties specified above, that allows their application a luminescent additive to ink for the hidden marking of valuables. The said compounds also belong to the class of REE mixed ligand complexes.

The structural formula of the claimed compounds is as follows:

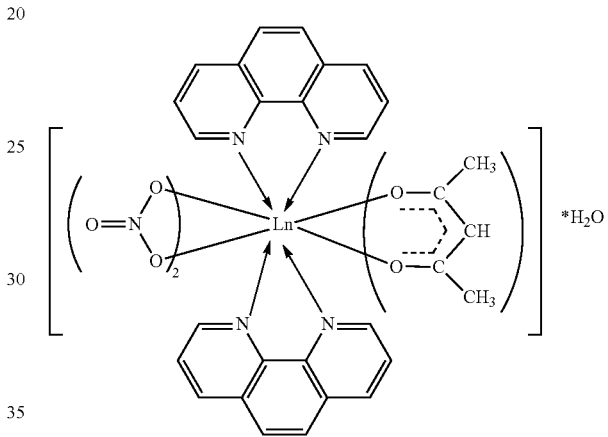

The claimed compounds are applicable for use as a luminescent additive to ink for the hidden marking of valuables. Thus, the proposed luminescent additive to ink is the compound consisting of di-(nitrate)acetylacetonatobis (1,10-phenanthroline) lanthanide (III) with the general formula $[Ln(NO_3)_2Acac(Phen)_2]*H_2O$, where Ln is $Tb_xEr_{1-x}$, Acac is acetylacetonate-ion, Phen is 1,10-phenanthroline, and is characterized by three protective features controllable in automatic mode independently from each other.

The first protective feature is represented by the capability of demonstrating luminescence in green light under the influence of UV-radiation. The second protective feature is represented by capability of demonstrating luminescence in green light under the influence of X-rays (Roentgen luminescence). The third protective feature is represented by capability of demonstrating thermo-luminescence, that is, the capability of accumulating, for indefinite period of time, the energy of UV- and X-ray radiation and to flash in green light emission in the course of subsequent heating. All listed features can be automatically controlled that allows application of the said compounds for hidden marking of valuables for protection against forgery.

Presence of three independent protective features allows identifying univocally valuables and offers the effective level of their protection.

The claimed compounds, their properties and method of their production have not been described in scientific and technical publications.

The claimed new chemical compounds are produced in acid medium at interacting of oxides of Tb and Er lanthanides dissolved in the diluted hydrogen nitrate, and alcohol solutions of organic ligands taken in a stoichiometric ratio.

To produce the compound with the preset ratio of terbium and erbium it is necessary to ensure interacting the sum of terbium nitrates and erbium with acetylaceton and 1,10-phenanthroline in strictly preset ratio 1:2:2 accordingly, in acid aqua-ethanol medium at pH 1-2.5. Then pH of the reaction medium is increased up to 6, 5-7 and is kept in that state for the period of 20 to 40 minutes and thereafter the target product is extracted using known methods.

The experiments show, that the optimum pH values for sedimentation of the target product are 6.5 to 7, a deviation from the said value results in a decrease of the target product yield: at, pH below 6.5 the output drops because of incomplete sedimentation of the complex, and at pH over 7, a partial hydrolysis of the target product takes place. The sediment in the form of a white deposit is then washed out by the aqua-ethanol mixture and is dried in a vacuum desiccator over $CaCl_2$.

The individuality of the produced compounds has been determined on the basis of the element analysis, IR-spectroscopy, luminescent spectroscopy, X-ray crystal analysis.

The samples have been subjected to X-ray bombarding radiation by means of apparatus URS-01 (25 kV, 20 mA, the Ni-anticathode) through a window made of beryllic foil and to UV-irradiation act (not filtrated light from the mercury lamp DRT-250).

X-ray patterns of new compounds have been filmed by the diffractometer DRON 2.0 in $CuK_\alpha$-radiation. Comparison of the produced mixed metals complexes Tb and Er with $Ln(NO_3)H_2O$, $Ln(AA)_3Phen$ and other analogues confirms the individuality of new compounds and indicates absence of impurities in the original compounds.

X-ray patterns of the compounds produced as a result of iterative (repeated) synthesis, have been reproduced.

Infra-red spectrums of absorption of the claimed compounds have been registered on spectrophotometer Perkin-Elmer 522 within the wave range of 400-4 000 $cm^{-1}$. Samples for shooting have been prepared in the form of suspensions in liquid petrolatum. The results of IR spectroscopy indicate the bi-dentate nature of coordination of $NO_3$ groups (magnitude of splitting $/v_1-v/$ makes 180 $cm^{-1}$). Coordination of 1,10-phenanthroline has been confirmed by splitting of a strip of deformation vibrations DVib in the area of 850 $cm^{-1}$ to 850 and 865 $cm^{-1}$ (Spacu P. et al., Rev. Roum. Chim., 1972, V.17, N4, p. 697).

Low-temperature luminescence spectrums have been registered on SDL-1 device. Radiation has been provided by the mercury lamp DRSh-250.

Luminescence spectrums of new compounds considerably differ, by their character of splitting the strips and distributing intensities, from the spectrums of the earlier known terbium acetylacetonate and erbium acetylacetonate with phenanthroline 1,10. The most intensive line in the luminescence spectrum of the claimed compounds, which is responsible for over 90% of radiation, matches to transfer of terbium ion $^5D_4$-$^7F_5$. Half-width of a line makes about 3 nanometers that ensures pure green light radiation of with high intensity and, accordingly, considerably increases possibility of univocal identification of a luminescent label (marker).

Decoded by X-ray crystal analysis method the crystalline structure of the claimed compound of di-(nitrate)acetylacetonatobis (1,10-phenanthroline) lanthanide (III) with the general formula $[Ln(NO_3)_2Acac(Phen)_2]*H_2O$, where Ln is $Tb_xEr_{1-x}$, univocal indicates the absence of 1,10-phenanthroline in the structure of toned outer sphere cation (unlike known most similar compounds described in the inventor's certificate SU No 16797 69 for which the structural formula, for comparison, is reproduced further).

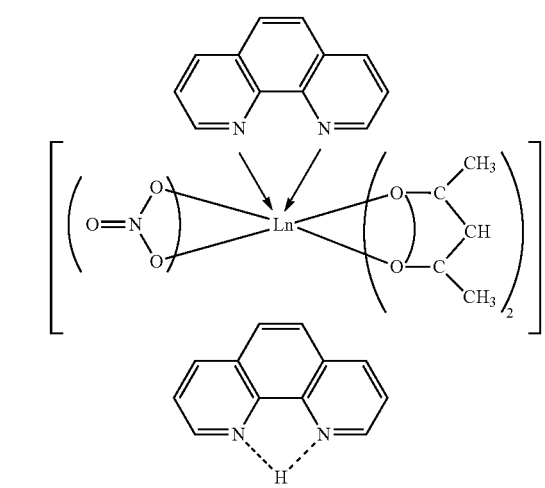

Besides, other structural differences between the claimed and known compounds are observed, such as: only one molecule of acetylaceton is presented in the claimed compound (instead of two compounds in the prototype), two molecules of 1,10-phenanthroline, coordinated to metal, are presented (instead of one in the prototype), molecule of water is presented, as well as erbium (III) ion-co-activator (absent in the prototype).

The change of composition and structure of the claimed compounds results in substantial improvement of characteristics of luminescent additives.

Thus, the reports of the performed chemical, element, X-ray phase and fluorometric analysis, IR spectroscopy and the direct method of X-ray crystal analysis do univocally confirm appearance of the new chemical combinations corresponding to the above structural formula.

The invention task is also solved by producing ink for the hidden marking of the valuables, containing the proposed luminescent additive in the sufficient quantity.

It was experimentally determined, that the sufficient quantity of the luminescent additive inducted into ink, lays within the range of 0.001 to 0.05 mass %.

At introduction of the claimed luminescent additive in ink in quantity less than 0.001 mass % at illumination by UV-light the applied label (marker) produces insufficient light intensity for Visual observation, whereas in quantity over 0.05 mass % the additive can hardly be dissolved because of the low solubility.

The proposed luminescent additive to ink can be applied to the hidden marking of valuables represented by documents, banknotes, securities, identification cards, chips-cards, passes and so forth, which require protection against forgery and falsification.

The technical results received at implementation of the claimed inventions, consist in production of new chemical compounds, and also in higher level of protection of the valuables against forgery due to introduction of three levels of protection which can be automatically controlled independently of each other (simultaneous presence of three independent physical properties in the same luminescence additive to ink, namely, intensive luminescence, X-ray luminescence and a thermo-luminescence).

DETAILED DESCRIPTION OF THE PREFERRED EMBODIMENTS

Example 1

This Example confirms possibility of producing the concrete compounds.

1 millimole (0.453 g) Tb(NO)*6H$_2$0 and 1 millimole (0.461 g) Er(NO)s*6H$_2$0 are dissolved in 5 ml of distilled water, 4 millimole (0.792 g) of 1,10-phenanthroline, dissolved in 15 ml of 96% ethanol, are added, and 4 millimole (0.400 ml) of acetylaceton are also added. Thus, the ratio of the initial components makes 1:2:2.

The solution is intensively agitated and HNO$_3$ is added drop-wise to reach pH 2, then 25% caustic ammonia is add drop-wise to reach pH 6. The fallen out fine-crystalline deposit is filtered off, washed out with 30 ml of aqua-ethanol mix (1:1) and is dried for one day on air. The target product output makes 71.5%.

According to the results of chemical, X-ray and luminescent analyzes the composition of the produced compound corresponds to the formula

[Tb$_{0.5}$Er$_{0.5}$(NO$_3$)$_2$Acac(Phen)$_2$]*H$_2$0 where Acac is acetylacetonate-ion, Phen is 1,10-phenanthroline.

Similarly, using the corresponding stoichiometrical ratio of Tb and Er, we have received the claimed compounds with other REE ratio.

The concrete compositions of the produced compounds and the relative intensity of their cold light (l$_{lum.}$) thermo-luminescence (S) and X-ray luminescences (R) are shown in Table 1. Examples 1 and 2 refer into to the compounds containing only terbium or only erbium; Examples 3 to 9 refer to claimed compounds with formula [Tb$_x$Er$_{1-x}$(NO$_3$)$_2$Acac(Phen)$_2$]*H$_2$O, and the Example 10 refers to the compound of the prototype.

It follows from Table 1, that, among the claimed compounds, one should prefer, by its features, the compound with formula [Tb$_{0.99}$Er$_{0.01}$ (NO$_3$)$_2$Acac(Phen)$_2$]*H$_2$O. Example 10 shows, that the intensity of thermo-luminescence demonstrated by the prototype compound, is low—approximately 2 to 6 times less than the same feature of the claimed compounds. The efficiency of cold light (luminescence) and X-ray luminescence oa the prototype compound does not attain the maximum intensity registered for the claimed compounds.

Example 2

This Example confirms possibility of the claimed compounds application in the capacity of the luminescent additive to ink for the hidden marking of valuables.

To apply the claimed compounds as a luminescent additive to such ink the compounds are, first, dissolved in suitable organic solvent (for example, dioxane, acetone). Acetone has proved to be an optimum dissolvent for the claimed compounds.

The produced solutions of the compounds with formula [Tb$_x$Er$_{1x}$(NO$_3$)$_2$Acac(Phen)$_2$]*H$_2$0 are applied in the form of a label on the marked polymeric or pulp-and-paper surface, are dried, the luminescent, X-ray luminescent and thermo-luminescent features are measured.

For this purpose a label (marker) is visualized by illuminating from sources of UV-radiation and X-rays, thus provoking emission of light in green range of light ($\lambda_{max}$=545 nanometer).

To enable the third level of protection, the marked sample is irradiates with UV- or X-rays at low temperatures, then the chilled sample is heated up and the intensity of a thermo-luminescence is measured. Further, identification of the document is performed the conclusion concerning its authenticity is made.

Application of solutions with the claimed luminescent additive has been checked on a number of polymeric carrying agents, in particular—on carrying agents made of polymethylmethacrylate (PMMA), polysterene (PS),polyvinylbutyral (PVB).

It was established, that the optimal results had been obtained for polyvinylbutyral (PVB), which samples marked by ink with the additive on the basis of composition [Tb$_{0.99}$Er$_{0.01}$(NO$_3$)$_2$Acac(Phen)$_2$]*H$_2$O, maintain the intensive luminescent, X-ray luminescent and thermo-luminescent properties, and also are photo-chemically resistant for a long time period.

The results of measurements of dependence of the relative intensity of luminescence on the concentration of the luminescent additive and the time period for polyvinylbutyral are presented in Table 2.

The Table 2 confirms that, in the studied interval of concentrations of [Tb$_{0.99}$Er$_{0.01}$(NO$_3$)$_2$Acac(Phen)$_2$]*H$_2$0, the intensity of luminescence of the compound linearly increases with the increase of concentration of the luminophore. In three months the intensity of the luminescence, practically, has not changed, besides, the thermo-luminescent properties has been maintained.

TABLE 1

| N | Connection | I$_{lum.}$ | S, % | R, % |
|---|---|---|---|---|
| 1 | [Tb(NO$_3$)$_2$Acac(Phen)$_2$]•H$_2$O | 100 | 100 | 100 |
| 2 | [Er(NO$_3$)$_2$Acac(Phen)$_2$]•H$_2$O | — | — | — |
| 3 | [Tb$_{0.5}$Er$_{0.5}$(NO$_3$)$_2$Acac(Phen)$_2$]•H$_2$O | 10 | 85 | 15 |
| 4 | [Tb$_{0.6}$Er$_{0.4}$(NO$_3$)$_2$Acac(Phen)$_2$]•H$_2$O | 10 | 73 | 15 |
| 5 | [Tb$_{0.8}$Er$_{0.3}$(NO$_3$)$_2$Acac(Phen)$_2$]•H$_2$O | 30 | 122 | 40 |
| 6 | [Tb$_{0.8}$Er$_{0.2}$(NO$_3$)$_2$Acac(Phen)$_2$]•H$_2$O | 50 | 163 | 60 |
| 7 | [Tb$_{0.9}$Er$_{0.1}$(NO$_3$)$_2$Acac(Phen)$_2$]•H$_2$O | 90 | 189 | 95 |
| 8 | [Tb$_{0.95}$Er$_{0.05}$(NO$_3$)$_2$Acac(Phen)$_2$]•H$_2$O | 95 | 239 | 100 |
| 9 | [Tb$_{0.99}$Er$_{0.01}$(NO$_3$)$_2$Acac(Phen)$_2$]•H$_2$O | 100 | 206 | 100 |
| 10 | (PhenH) [Tb(NO$_3$)$_2$AA$_2$Phen] (prototype) | 80 | 40 | 80 |

TABLE 2

| Polymeric Carrier | Solvent | Concentration of the Additive, Mass % | Intensity of the Luminescence of the Freshly Prepared Film | Intensity of the Luminescence of the Film After Three Months |
|---|---|---|---|---|
| PVB | Acetone | 0.0062 | 1.0 | 1.00 |
| | | 0.0121 | 3.92 | 2.73 |
| | | 0.0181 | 4.83 | 4.26 |
| | | 0.0238 | 9.98 | 9.68 |
| | | 0.0301 | 19.14 | 19.14 |

What is claimed is:

1. The compound of di-(nitrate) acetylacetonatobis (1,10-phenanthroline) lanthanide (III) of the general formula [Ln (NO$_3$)$_2$Acac(Phen)$_2$]*H$_2$O, where Ln is Tb$_x$Er$_{1-x}$, such that $0.5 \leq X < 1$, Acac is acetylacetonate-ion, and Phen is 1,10-phenanthroline, characterized in that it has the following structural formula:

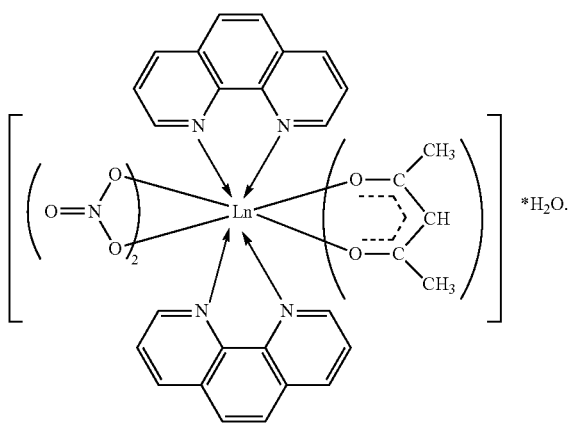

2. The compound as in claim 1, [Tb$_{0.99}$Er$_{0.01}$(NO$_3$)$_2$Acac(Phen)$_2$]*H$_2$O wherein Acac is acetylacetonate-ion, and Phen is 1,10-phenanthroline.

3. Ink for hidden marking the valuables, containing the luminescent additive represented by the compound of di-(nitrate) acetylacetonatobis (1,10-phenanthroline) lanthanide (III) of the general formula [Ln(NO$_3$)$_2$Acac(Phen)$_2$]*H$_2$O, where Ln is Tb$_x$Er$_{1-x}$, Acac is acetylacetonate-ion, Phen is 1,10-phenanthroline in the efficient quantity of 0.001 to 0.05 mass %, and $0.5 \leq X < 1$.

* * * * *